United States Patent [19]

Mueller et al.

[11] Patent Number: 5,766,163
[45] Date of Patent: Jun. 16, 1998

[54] CONTROLLABLE TROCAR FOR TRANSMYOCARDIAL REVASCULARIZATION (TMR) VIA ENDOCARDIUM METHOD AND APPARATUS

[75] Inventors: Richard L. Mueller; Stuart D. Harman, both of Sunnyvale, Calif.

[73] Assignee: Eclipse Surgical Technologies, Inc., Sunnyvale, Calif.

[21] Appl. No.: 675,732

[22] Filed: Jul. 3, 1996

[51] Int. Cl.$^6$ .............................................. A61B 17/36
[52] U.S. Cl. ................................................ 606/7; 606/15
[58] Field of Search ........................... 606/7, 9, 14–16, 606/180

[56] References Cited

U.S. PATENT DOCUMENTS

| | | | |
|---|---|---|---|
| 4,658,817 | 4/1987 | Hardy | 128/303.1 |
| 4,669,465 | 6/1987 | Moore et al. | 128/303.1 |
| 4,790,310 | 12/1988 | Ginsburg et al. | 128/303 |
| 5,114,403 | 5/1992 | Clarke et al. | 604/96 |
| 5,125,926 | 6/1992 | Rudko et al. | 606/19 |
| 5,188,634 | 2/1993 | Hussein et al. | 606/7 |
| 5,217,454 | 6/1993 | Khoury | 606/7 |
| 5,281,214 | 1/1994 | Wilkins et al. | 606/16 |
| 5,298,026 | 3/1994 | Chang | 606/16 X |
| 5,380,316 | 1/1995 | Aita et al. | 606/7 |
| 5,389,096 | 2/1995 | Aita et al. | 606/15 |
| 5,571,215 | 11/1996 | Sterman et al. | 606/7 X |
| 5,683,378 | 11/1997 | Christy | 606/1 |

OTHER PUBLICATIONS

Deckelbaum, "Cardiovascular Apps. of Laser Tech.", Lasers in Surgery and Medicine, 15:315–341 (1994).
Frazier et al., "Myocard. Revasc. with Las.", Cullen Cardio. Res. Labs., Tx. Heart Inst., Supp. II C vol. 92, No. 9, II–58–65 (Nov. 1, 1995).

Primary Examiner—Francis Jaworski
Attorney, Agent, or Firm—Ray K. Shahani; Janet Kasier Castaneda

[57] ABSTRACT

A minimally invasive surgical apparatus for providing access to the inside of a chamber of the heart for performing TMR on anterior and posterior walls therein. A unitary or a two piece trocar assembly is positioned through the chest wall. An obturator with a tissue piercing blade at one end is used to saw, pierce or otherwise cut a hole through the epicardium into and through myocardium. Once the trocar assembly extends into the heart chamber, a laser delivery device with deflection means is introduced into the chamber. Deflection or curvature of the end of the laser delivery device can be controlled by angulation control components, such that TMR channels can be created at various positions on the anterior and posterior walls of the chamber. Rotation control components for the fiber or other laser delivery devices will allow the surgeon to rotate the fiber once a predetermined deflection or curvature has been imparted to the distal end of the laser delivery device.

27 Claims, 13 Drawing Sheets

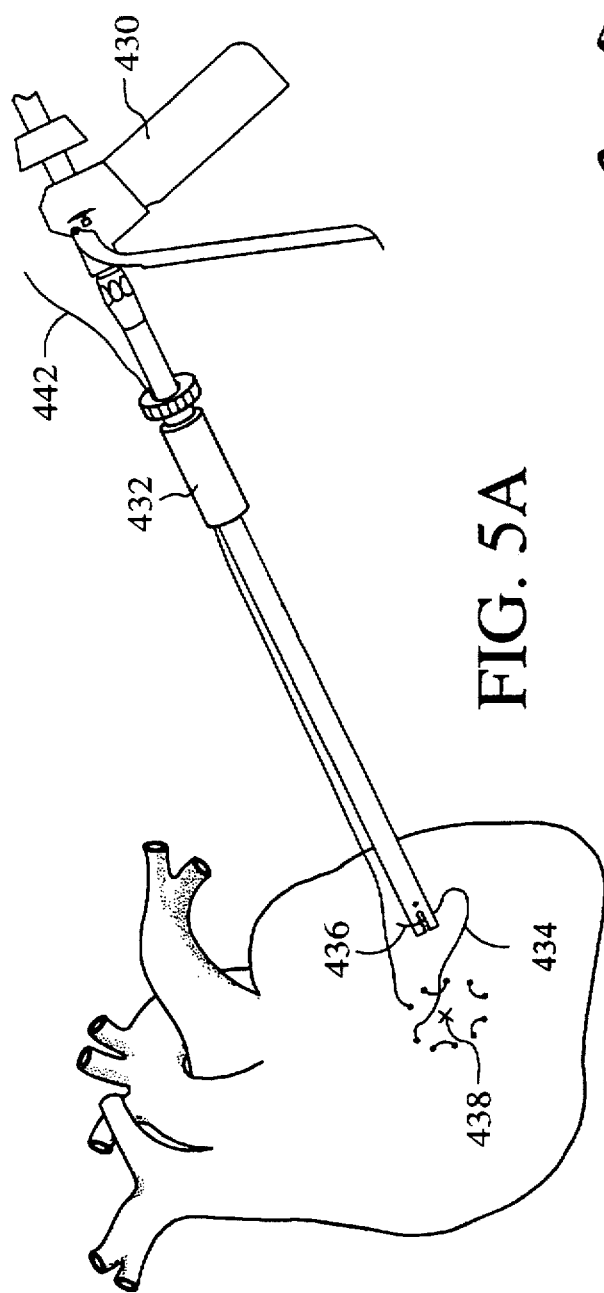
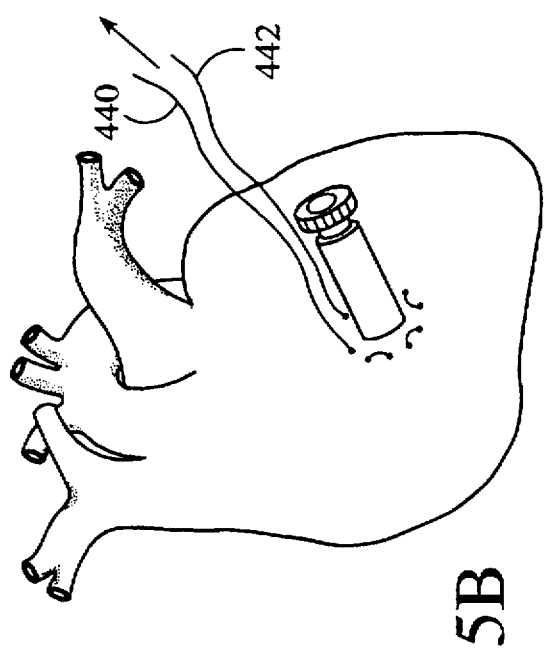
FIG. 5A
FIG. 5B

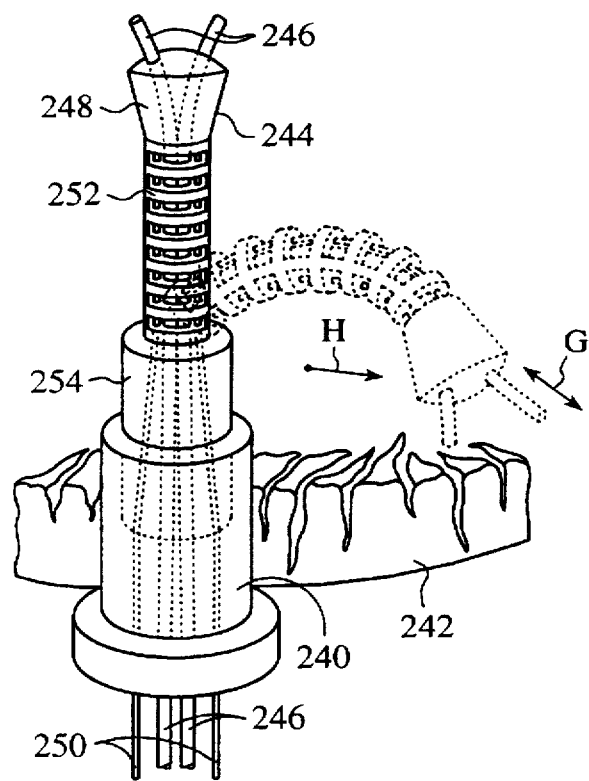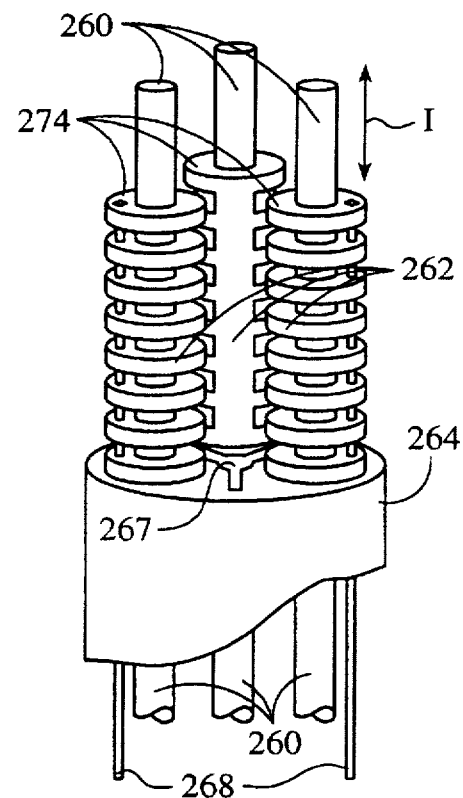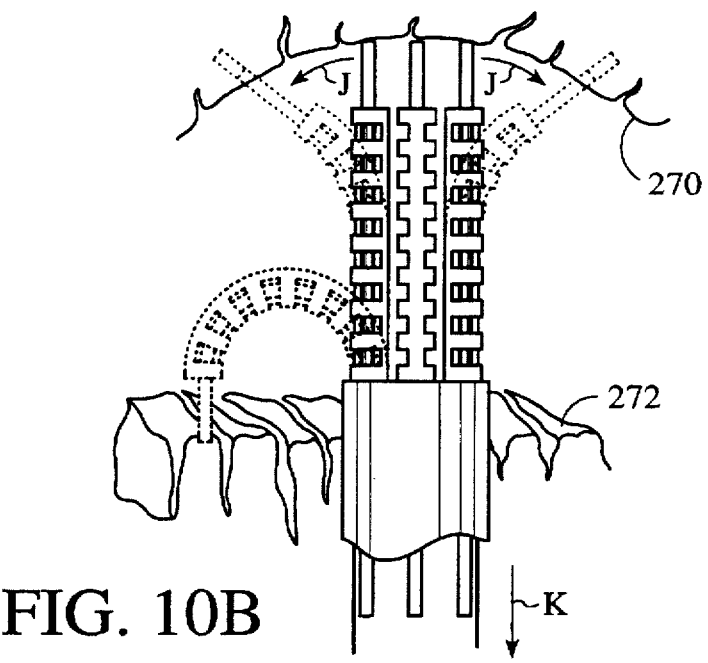

CONTROLLABLE TROCAR FOR TRANSMYOCARDIAL REVASCULARIZATION (TMR) VIA ENDOCARDIUM METHOD AND APPARATUS

FIELD OF THE INVENTION

The present invention relates to a surgical procedure known as laser-assisted transmyocardial revascularization (TMR), and more particularly, to a method and apparatus for performing such minimally invasive surgery (MIS) procedure using a trocar apparatus in conjunction with a controllable laser delivery means guide for creating TMR channels from the endocardium into myocardium.

BACKGROUND OF THE INVENTION

Heart disorders are a common medical problem in developed countries. The major cause of heart disease in developed countries is impaired blood supply. The coronary arteries, which supply blood to the heart, become narrowed due to atherosclerosis and part of the heart muscle is deprived of oxygen and other nutrients. The resulting ischemia or blockage can lead to angina pectoris, a pain in the chest, arms or jaw due to a lack of oxygen to the heart, or infarction, death of an area of the myocardium caused by the ischemia.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be treated in a number of ways. Drug therapy, including nitrates, beta-blockers, and peripheral vasodilatator drugs (to dilate the arteries) or thrombolytic drugs (to dissolve clots) can be very effective. Transluminal angioplasty is often indicated—the narrowed diameter of the opening or lumen of the artery, clogged with atherosclerotic plaque or other deposits, can be increased by passing a balloon to the site and inflating it. In the event drug therapy is ineffective or angioplasty is too risky, the procedure known as coronary artery bypass grafting (CABG) may be indicated. The procedure requires the surgeon to make an incision down the center of the patient's chest and the heart is exposed by opening the pericardium. A length of vein is removed from another part of the body, typically the leg. The section of vein is first sewn to the aorta and then sewn onto a coronary artery at a place such that oxygenated blood can flow directly into the heart. CABG is a major surgical procedure which requires the installation of the heart-lung machine and the sternum must be sawed through.

Another method of improving myocardial blood supply is called transmyocardial revascularization (TMR), the creation of channels from the epicardial to the endocardial portions of the heart. The procedure using needles in a form of "myocardial acupuncture" has been used clinically since the 1960s. Deckelbaum. L. I., Cardiovascular Applications of Laser technology, *Lasers in Surgery and Medicine* 15:315–341 (1994). The technique was said to relieve ischemia by allowing blood to pass from the ventricle through the channels either directly into other vessels perforated by the channels or into myocardial sinusoids which connect to the myocardial microcirculation. The procedure has been likened to transforming the human heart into one resembling that of a reptile.

In the reptilian heart, perfusion occurs via communicating channels between the left ventricle and the coronary arteries. Frazier, O. H., Myocardial Revascularization with Laser—Preliminary Findings, *Circulation*, 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR using lasers to bore channels in the myocardium. Histological evidence of probable new vessel formation adjacent to collagen occluded transmyocardial channels exists. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the lumen of the laser channels is or can become hemocompatible and that it resists occlusion caused by thrombo-activation and/or fibrosis. A thin zone of charring occurs on the periphery of the laser-created transmyocardial channels through the well-known thermal effects of optical radiation on cardiovascular tissue.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforates a portion of tissue to provide the laser beam direct access to distal tissue.

U.S. Pat. No. 5,125,926 issued Jun. 30, 1992 to Rudko et al. teaches a heart-synchronized pulsed laser system for TMR. The device and method comprises a device for sensing the contraction and expansion of a beating heart. As the heart beat is monitored, the device triggers a pulse of laser energy to be delivered to the heart during a predetermined portion of the heartbeat cycle. This heart-synchronized pulsed laser system is important where the energy and pulse rate of the particular type of laser are potentially damaging to the beating heart or it's action. Application of laser energy to a beating heart can induce fibrillation or arrhythmia. Additionally, as the heart beats, the spatial relationship between the heart and the tip of the laser delivery probe may change so that the necessary power of the beam and the required position of the handpiece may be unpredictable.

U.S. Pat. Nos. 5,380,316 issued Jan. 10, 1995 and 5,389,096 issued Feb. 14, 1995 both to Aita et al. teach, respectively, systems and methods for intra-operative and percutaneous myocardial revascularization. The '316 patent is related to TMR performed by inserting a portion of an elongated flexible lasing apparatus into the chest cavity of a patient and lasing channels directly through the outer surface of the epicardium into the myocardium tissue. In the '096 patent TMR is performed by guiding an elongated flexible lasing apparatus into a patient's vasculature such that the firing end of the apparatus is adjacent the endocardium. Channels are created directly through the endocardium into the myocardium tissue without perforating the pericardium layer.

TMR is most often used to treat the lower left chamber of the heart. Distal coronary arteries, which are more prone to blockage and resulting heart muscle damage, are supplied with blood from the left ventricle.

To date, TMR channels have been created surgically either through the epicardial surface into the myocardium, or in the alternative, vascularly via catheter from an endocardium wall within a chamber radially outwards into myocardium. In the latter case, accessing a heart chamber typically requires a vascular approach, such as via femoral artery, using more complicated catheter equipment and more sophisticated methodology. Modern surgical methods permit less traumatic surgical access to the heart using minimally invasive techniques.

Thus, it is an object of the present invention to provide a controllable trocar for MIS access to perform TMR via endocardium method and apparatus.

It is a further object of the present invention to provide a trocar apparatus which can be placed in the heart at a predetermined position and which will effect revascularization of myocardium via the endocardium at preselected locations on the endocardium.

It is a further object of the present invention to provide a trocar apparatus with controllable fiber guide orientation means for effecting TMR via the endocardium.

It is a further object of the present invention to provide a method for performing TMR channeling of myocardium via the endocardium in which access to the endocardium is gained via controllable trocar apparatus suitable for MIS procedures.

SUMMARY OF THE INVENTION

A minimally invasive surgical apparatus for providing access to the chambers of the heart for performing procedures therein, the apparatus comprising trocar means for insertion through a chest wall and into a myocardial layer of the heart, at least one laser delivery means for insertion through the trocar means and through the myocardial layer into a chamber of the heart, the at least one laser delivery means having a distal end for delivering laser energy to perform the procedure, and guide means operatively associated with the at least one laser delivery means for orienting the at least one laser delivery means to direct laser energy within the chamber to perform a minimally invasive surgical procedure therein. The surgical apparatus further comprises tissue piercing means for cutting an opening in an epicardial layer of the heart for insertion of the trocar means into the myocardial layer. In a preferred embodiment, the trocar means further comprises proximal and distal ends, the proximal end for positioning on the outside of the chest wall defining a cavity for removable fluid seal means, the distal end for insertion into the myocardial layer, and a hollow tubular portion extending between the proximal end and the distal end and defining a pathway from the outside of the chest wall into the chamber. In a preferred embodiment, at least one region of the hollow tubular portion of the trocar means is flexible. In a preferred embodiment, the trocar means comprises a chest wall portion and a heart portion, the chest wall portion for positioning on and insertion through a chest wall and having a opening extending therethrough, and the heart portion having a predetermined geometry permitting to it to fit slidingly through the opening through the chest wall portion for insertion into and through the myocardial layer of the heart. In a preferred embodiment, the heart portion defines a fluid seal means for preventing loss of fluid from the heart chamber. In a preferred embodiment, the chest wall portion of the trocar means is physically separable from the heart portion of the trocar means. In a preferred embodiment, the at least one laser delivery means comprises at least one optical fiber. In a preferred embodiment, the guide means comprises at least one curved rotatable tube surrounding the at least one laser delivery means and extendable beyond the distal end of the trocar means. In a preferred embodiment, the curved tube comprises a shape memory material. In a preferred embodiment, the guide means comprises an articulating portion extending beyond the distal end of the trocar means, the articulating portion having proximal and distal ends, the proximal end adjacent the distal end of the trocar means, and control means for causing the articulating portion to bend, thereby orienting the laser delivery means to direct laser energy toward at least one preselected portion of endocardium. In a preferred embodiment, the laser delivery means is disposed within the articulating portion of the guide means, the distal end of the laser delivery means extendable beyond the distal end of the articulating portion. In a preferred embodiment, the control means of the guide means comprises at least one steering wire, pushing and pulling on the at least one steering wire causing the articulating portion to bend, thereby orienting the laser delivery means to direct laser energy toward at least one preselected portion of endocardium. In a preferred embodiment, wherein the guide means comprises at least one rotatable, hollow tube surrounding the laser delivery means, the laser delivery means having a distal end pre-bent into a curved position within the hollow tube, the distal end maintaining the curved position when advanced out of the hollow tube into the heart chamber. In a preferred embodiment, the tissue piercing means is retractable into the trocar portion. In a preferred embodiment, the guide means further comprises at least one extendible, deflectable shaft means surrounding the laser delivery means. In a preferred embodiment, the surgical apparatus further comprises fiber rotation control means for controlling the angular rotation of the laser delivery means. In a preferred embodiment, the surgical apparatus further comprises fiber angulation control means for controlling the orientation of the distal end of the laser delivery means. In a preferred embodiment, the surgical apparatus further comprises a handle portion, the handle portion having fiber rotation control means and fiber angulation control means.

A minimally invasive surgical method for performing a medical procedure initiated at an endocardial surface of a heart chamber, the method comprising the steps of placing a trocar device through an opening in the chest wall, creating a trocar opening at a selected position on the outer surface of the heart, placing the trocar device through myocardium and into the heart chamber, extending at least one laser delivery device through the trocar into the heart chamber, and delivering laser energy from the at least one laser delivery device to complete the medical procedure. In a preferred embodiment, the method further comprises the step of suturing the trocar opening prior to placing the trocar device into the heart chamber. In a preferred embodiment, the method further comprises the step of advancing the laser delivery means through the heart chamber, across a heart valve, and into an adjacent heart chamber. In a preferred embodiment, the step of delivering laser energy includes delivering sufficient energy to form a plurality of channels extending from the endocardium into the myocardium.

A trocar for performing minimally invasive surgery (MIS) on the heart, the trocar comprising a proximal end adapted to protrude outwardly from a chest wall and defining a cavity for removable fluid seal means, a distal end defining means for penetrating an epicardial layer of the heart for inserting the distal end through myocardium and into a heart chamber, and hollow connector means extending between and connecting the proximal and distal ends and for permitting passage of surgical tools from outside the chest wall into the chamber.

Numerous other advantages and features of the present invention will become readily apparent from the following detailed description of the invention and the embodiments thereof, from the claims and from the accompanying drawings.

BRIEF DESCRIPTION OF THE DRAWINGS

FIGS. 5A and 5B are representative views of methods and apparatus for placing a purse string suture in the heart prior to positioning an inner trocar in the heart.

FIG. 9 is a representative perspective view of a twin fiber single body controllable guide means and trocar apparatus of the present invention.

FIGS. 10A and 10B are representative perspective views of a multi-guide means TMR trocar apparatus of the present invention.

DETAILED DESCRIPTION OF THE PREFERRED EMBODIMENT

The present invention is intended for use with any medical laser. In particular, a Holmium or excimer type laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers, rods, mirrors configurations and other laser delivery means are well described and will be useful in practicing the methods of this invention. It will also be understood that the preferred methods of the present invention are performed using the novel and unique devices described herein as well as any conventional mechanisms enabling angling or rotation of the laser delivery means to effect creation of the channels.

TMR is performed most often and most successfully in myocardium of the left ventricle, the largest chamber of the heart. The left ventricle is the largest chamber in the heart receiving and pumping oxygenated blood through the body.

It will be understood that novel procedures and apparatus of the present invention are exceptionally well suited for use in what has of late come to be referred to as minimally invasive surgery. It will further be understood that the scope of the novel methods and apparatus described herein will include such procedures as well as surgical and catheter procedures.

Figure 1:
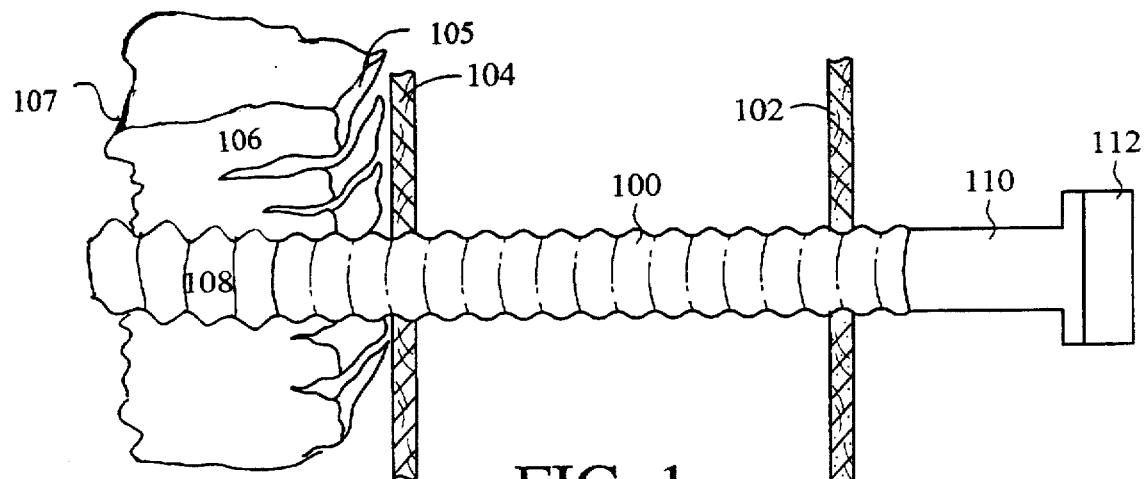
FIG. 1 is a representative view of a preferred embodiment of a flexible, unitary trocar apparatus of the present invention.

FIG. 1 is a representative view of a preferred embodiment of a flexible, unitary trocar apparatus of the present invention. The apparatus comprises a flexible trocar portion 100 which is positioned in the chest wall 102 of the patient, through the pericardial sac 104, the epicardial surface 105, the myocardium 106 and the endocardium 107. The distal end 108 extends into the heart chamber itself while the proximal end 110 will be equipped with a removable blood seal means 112 to prevent undesired blood loss during the various steps of the procedure.

Figure 2A:
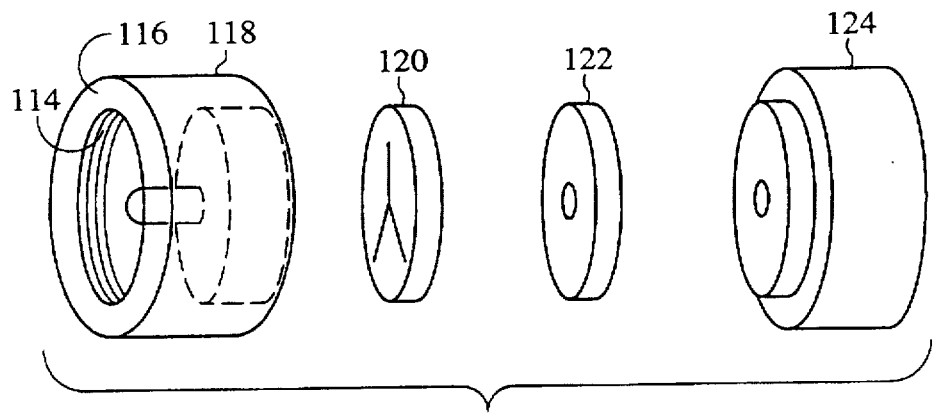
FIG. 2A is a preferred embodiment of a typical blood seal means used in the apparatus of the present invention.

FIG. 2A is a preferred embodiment of a typical blood seal means used in the apparatus of the present invention. Fastening means 114 on the distal end 116 of the assembly, such as threads or bayonet type mount are provided in the inner housing portion 118 to connect the assembly to the proximal end of the trocar apparatus. Inside the inner housing portion a rubber or other elastic, flexible material rubber slit seal 120 stops blood flow when no obturator or other tool is in place. A round circle seal 122 helps to stop blood flow around the shaft of the tool when in place. An end cap 124 retains the seal components within the assembly. It will be understood that an obturator will include a tissue piercing means, a laser delivery means such as a fiber optic or fiber bundle, other visualization means, etc., and will be known to those skilled in the art.

Figure 2B:
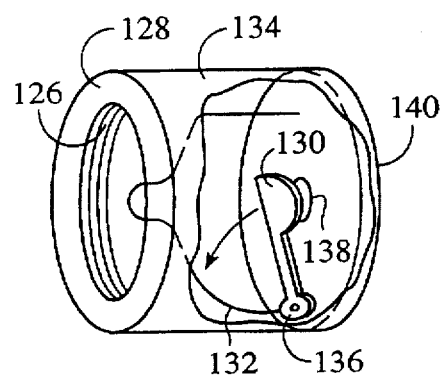
FIG. 2B is another preferred embodiment of a typical blood seal means used in the apparatus of the present invention.

FIG. 2B is another preferred embodiment of a typical blood seal means used in the apparatus of the present invention. Fastening means 126 on the distal end 128 of the blood seal means allows the blood seal assembly to be threaded or otherwise attached to the trocar apparatus. A hinged door member 130 is attached to the inside wall portion 132 of the housing portion 134 at hinge means 136. Thus, as blood enters the housing portion through the central opening, the door is pushed closed to plug a circle seal 138 at the proximal end 140 of the seal housing. However, when an obturator or other tool is introduced to the housing via the proximal end, the door is rotated out of the way of the tool and blood flow is prevented by forming a seal between the shaft of the tool and the circle seal.

In the preferred embodiments, the blood seal means are removable. More specifically, during atrial access, since blood pressure is low, a simple fluid column of between about 6 and about 12 inches will suffice to prevent undesired blood loss. In cases of ventricular access, higher internal blood pressure will create the need for an auxiliary blood seal means, as described above.

Figure 3:
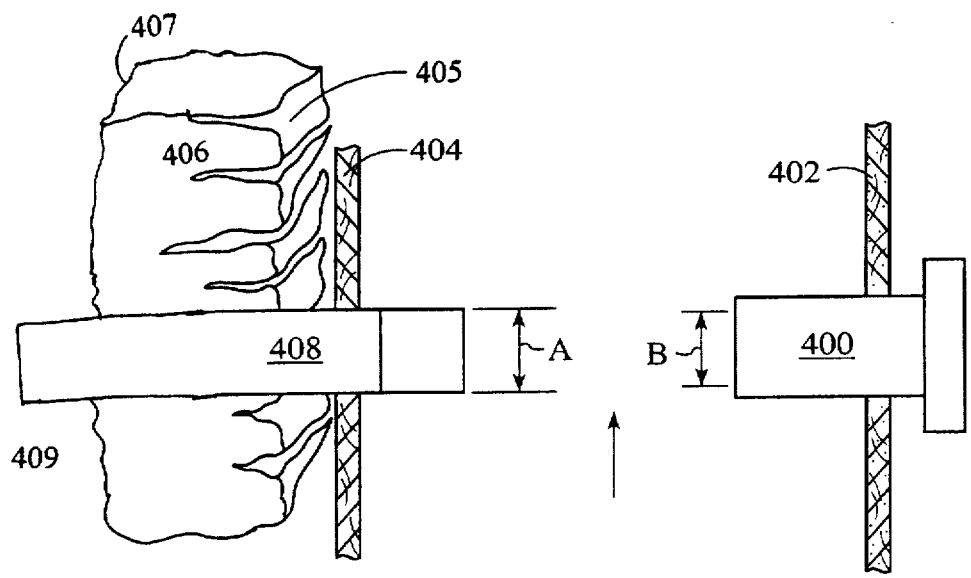
FIG. 3 is a representative view of a two-piece trocar apparatus of the present invention.

FIG. 3 is a representative view of a two-piece trocar apparatus of the present invention. An outer trocar portion 400 (or chest wall portion) is positioned through the chest wall 402. An obturator means is used to pierce the pericardial sac 404, the epicardium 405, the myocardium 406 and the endocardium 407. Thereafter, an inner trocar portion 408 (or heart portion) is positioned inside the hole into the chamber 409. It will be understood that the outer diameter A of the inner trocar portion is somewhat smaller in diameter that the inside diameter B of the outer trocar portion. In this embodiment, the utility of a blood seal means on the outer trocar portion is limited. However, a blood seal means on the inner trocar portion is highly useful. Alignment of the inner and the outer trocar portions can be done either visually or with an alignment tool.

Figure 4A:
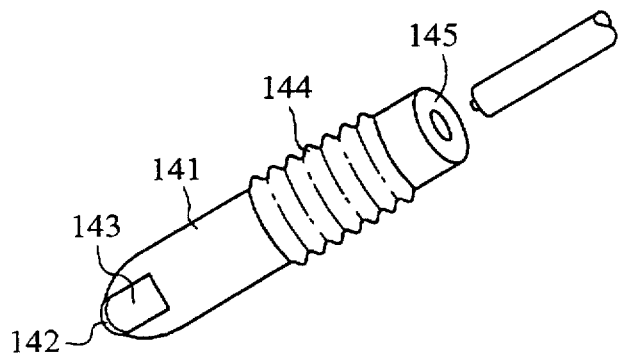
FIG. 4A is a representative view of a preferred embodiment of an obturator means with needle piercing means of the present invention.

FIG. 4A is a representative view of a preferred embodiment of an obturator means with tissue piercing means of the present invention. It is understood that this obturator means may be an independent device or may be built in and integral with a flexible or rigid trocar assembly. As described above, the obturator 141 is placed directly into the heart muscle. A tissue piercing means 142 is provided at the distal end 143. A preferred embodiment of the obturator comprises a flexible, externally ribbed shaft 144 to aid in holding the trocar in place in the heart wall. The obturator 141 is extendable and retractable. In a preferred embodiment of the present invention the obturator 141 is removable or displaceable within the trocar portion. The tissue piercing means 142 comprises a small razor-sharp rounded cutting edge having a predetermined size and thickness. To pierce through the heart into a chamber, the tissue piercing means on the obturator is extended through an outer trocar portion in the chest wall and used to create a central opening into the heart. As the opening is created, the trocar portion is also pushed into the opening, essentially displacing the tissue surrounding the pierce in the interconnecting matrix of myocardium. The tissue piercing means is a flat or curved blade being sharpened on one or both sides. In the preferred embodiment, the tissue piercing means is curved and attached to the obturator.

Figure 4B:
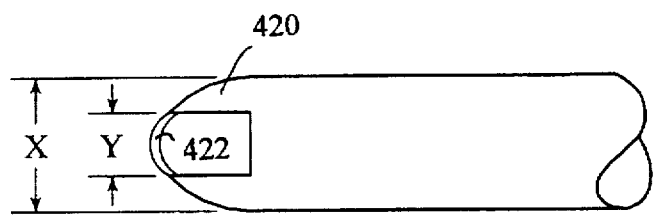
FIG. 4B shows the tip of a preferred embodiment of a tissue piercing means of the present invention.

FIG. 4B shows the tip of a preferred embodiment of a tissue piercing means of the present invention. The rounded, blunt distal end 420 has a predetermined width X. An inner sharpened blade 422 has a predetermined width Y. It will be observed that since Y is somewhat smaller than X, the motion of the blade being sawed or rocked back and forth to create a pierce or slit in the tissue will tend to dilate the tissue thereby having a sealing effect between the pierce and the blunt portion of the tissue piercing means and obturator.

Figure 4C:
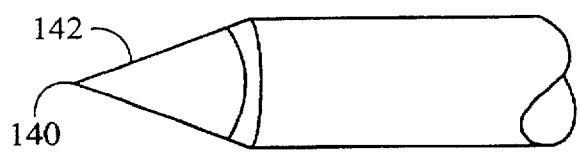
FIG. 4C is a representative perspective view of a preferred embodiment of the tissue piercing means of the present invention.

FIG. 4C is a representative perspective view of a preferred embodiment of the tissue piercing means of the present invention. The tissue piercing means has a distal tip 140. A flat blade portion 142 extends therefrom to pierce or slice the tissue. The tissue piercing means of the obturator can be removed and replaced with the laser delivery means and, optionally, other apparatus. It will be understood that various embodiments of the obturator and associated tissue piercing means are possible. The cutting blade can either be removed entirely from the trocar portion or the blade can be positioned or repositioned within the trocar portion such that it is safely out of the way of the laser delivery means and other structures to be placed inside the trocar portion or heart chamber. The cutting blade can be extended and otherwise manipulated so as to pierce the heart and gain entrance to the heart chamber. This cutting must be initiated at a predetermined position on the outer surface of the heart at a position which will be most operative. In a preferred method, boring into the heart through coronary structures will be avoided to minimize external bleeding but coronary structures can be pierced if appropriate consideration and safeguard against unwanted bleeding is taken and necessary suturing or other sealing means after withdrawal of the trocar portion through the heart muscle is used, if and as necessary.

FIGS. 5A and 5B are representative views of methods and apparatus for placing a purse string suture in the heart prior to positioning an inner trocar in the heart. A MIS suturing means 430 is placed through a chest wall trocar 432 in position. Common or other suture material 434 can be used. A needle 436, typically curved, is used to thread the suture material through the heart muscle in a circular pattern surrounding the inner trocar intended penetration site 438. The suture material is left in place with both the end attached to the needle and the distal end 442 extending therefrom. Thereafter, the suturing means and needle are removed and the tissue piercing means of the obturator is positioned on top of the heart muscle with the distal tip of the cutting blade placed at the inner trocar intended penetration site. After the tissue is pierced and the inner trocar is positioned inside the chamber, the purse strings can be tightened around the inner trocar to prevent blood loss during TMR. Once TMR is effected on the posterior and anterior surfaces of the inner chamber, the TMR tool and inner trocar portions are withdrawn. Finally, the purse string suture is tightened completely and the hole through the myocardium is closed completely and efficiently. This purse string suture prevents additional blood loss and will facilitate healing of the trocar hole.

Figure 5C:
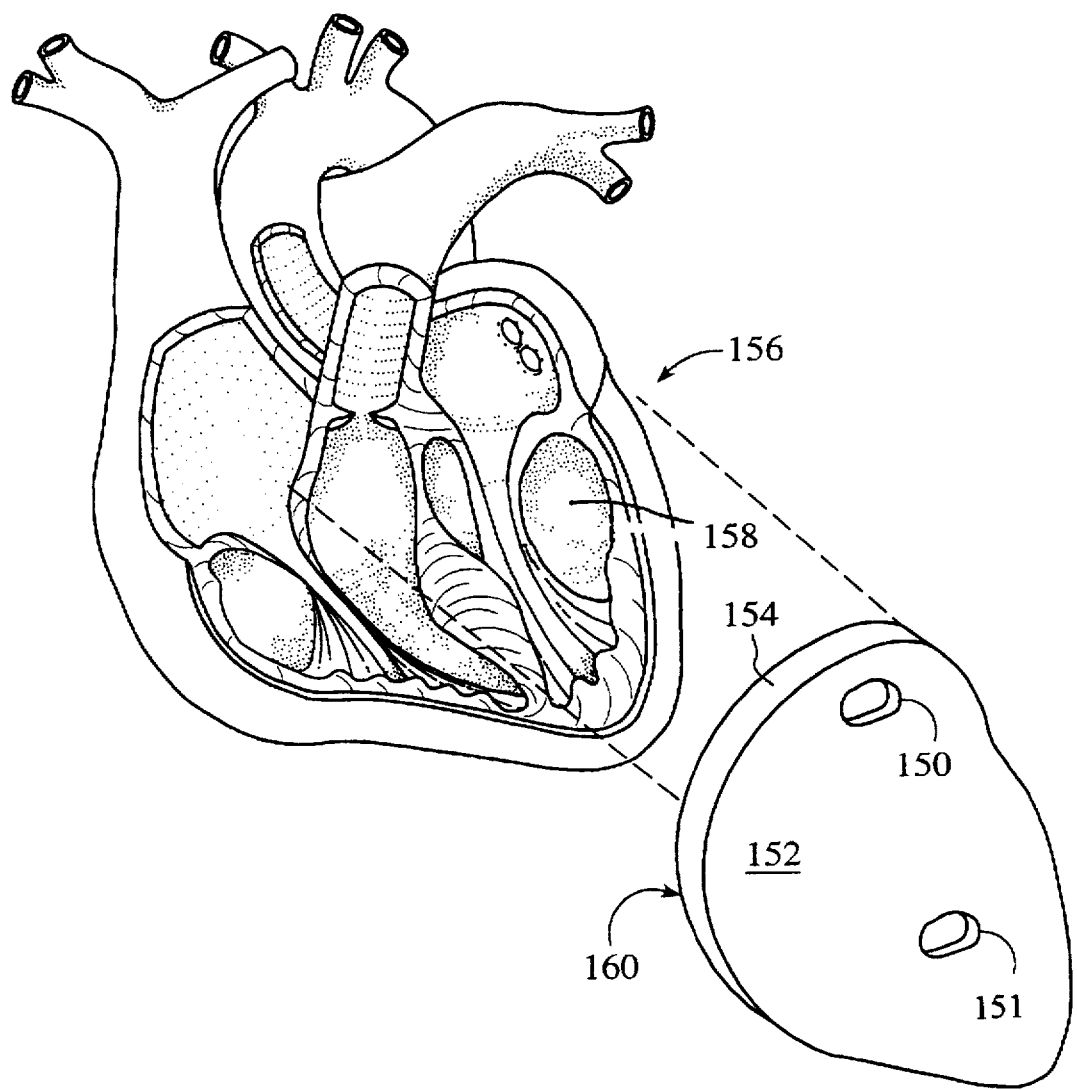
FIG. 5C is a representative perspective view of a partially resected human heart.

FIG. 5C is a representative perspective view of a partially resected human heart. This view shows the anatomy of the human heart relative to the TMR method and apparatus described herein. As shown, several placement sites, 150 and 151, may be made at a predetermined position on the epicardial surface 152 of the heart. As shown, site 150 will provide atrial access while site 151 will provide ventricular access. The trocar channel passes through myocardium 154 into the left atrium or the left ventricular chamber 156. It will be understood that the trocar site can be made in the front portion of the left ventricle, as shown, which will allow the surgeon to bore TMR channels both on the posterior wall 158 as well as on the anterior wall 160 with the method and apparatus of the present invention. An atrial placement allows for easier physician access, lower ambient blood pressure and a gentler fiber bend radius may be used. Atrial placement may also necessitate crossing the mitral valve.

It will be understood, however, that the trocar site may be placed on the rear portion of the left ventricle, providing that access thereto is possible, or directly from the side. When the trocar is placed on the side of the left ventricle directly across from the septum, i.e. the structure dividing the heart muscle into the right chambers and the left chambers, boring TMR channels straight through the septum may not be desirable in all cases. Generally, the surgeon will strive to avoid boring channels or mechanically disturbing in any way the aortic valve, the mitral valve or the cordae or tissue strands which attach to and control the leaflets of the heart valves. As mentioned above, while the left ventricle has been that portion of the heart which has been the subject of TMR study and practice in the past, these methods and apparatus will be available for use on any structure in the human body, their efficacy depends on the suitability of the treatment plan for the particular patient.

Preferred embodiments of fiber optic laser delivery devices suitable for use with the trocar apparatus described above are discussed below.

Figure 6A:
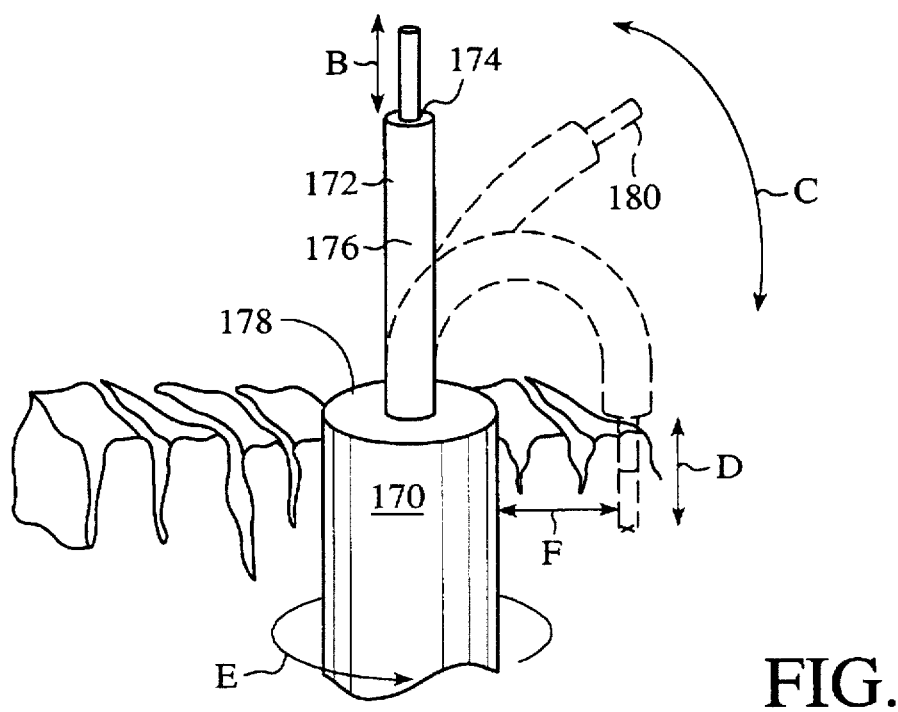
FIG. 6A shows a representative perspective view of a single laser delivery means inside a controllable guide means of the present invention.

FIG. 6A shows a representative perspective view of a single laser delivery means inside a controllable guide means of the present invention. From through the inner trocar portion 170 a controllable guide means 172 is inserted or extended. From within the controllable guide means 172, a laser delivery means 174 can be further extended in direction B for creating TMR channels in a posterior wall or other endocardial surface. The controllable guide means 172 has a curvature at one end. In a preferred embodiment, as the distal end 176 of the guide means is extended past the distal end of the trocar portion 178, a curvature of the guide means tends to deflect the distal end 180 of the laser delivery means in direction C. In this configuration, the laser delivery means can then be extended in direction D to create channels in an anterior wall or other endocardial surface. Furthermore, once a single channel is drilled through endocardium into myocardium, the guide means can be rotated in direction E to re-orient the laser delivery end of the laser delivery means. Thus, a second and/or additional TMR channels can be produced at essentially the same radial distance from the initial trocar placement site shown as distance F.

It will be understood that the curvature of the guide means can be implemented in various ways, which will be apparent to those skilled in the art. One such embodiment will be manufactured utilizing a guide means with a certain "memory" or preformed curvature. Plastic or metal or other suitable materials and methods for manufacturing components therefrom exist which can be extended through a straight trocar assembly but which, when extended completely therethrough, will develop a curvature when not restricted by a narrow, enveloping structure. Plastics, polymeric and other material tubing can be extruded with a predetermined, elastic, form retaining curvature. A suitable metal which has these memory-retaining properties is nitinol. The same self-curving properties can be imparted to braided mesh-type materials as well. Preferred embodiments also include bimetallic strips extending through the guide means or other channel structure defining the curvature of the laser delivery means within the heart chamber. As is well known, these and other materials tend to change their shape in a predetermined way when, for example, a certain electrical potential or charge is passed through one or more of the materials. This change in shape is a function of various physical properties of the materials used and their combination, these physical properties including thermal and potentiometric expansion, etc.

Figure 6B:
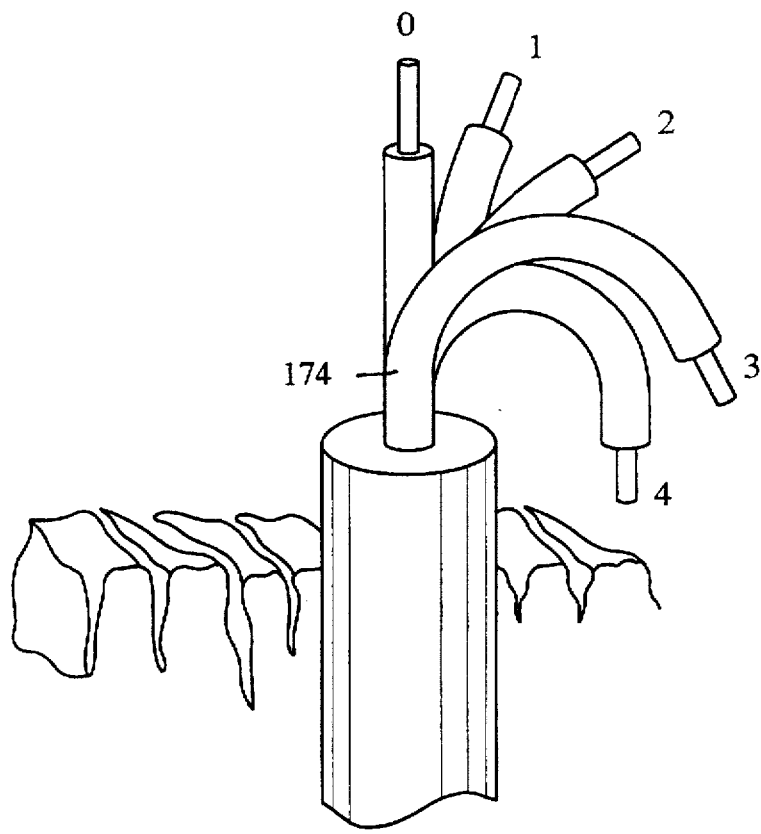
FIG. 6B is a representative cross sectional view of five relative positions of deflection of the laser delivery means of the present invention.
Figure 6C:
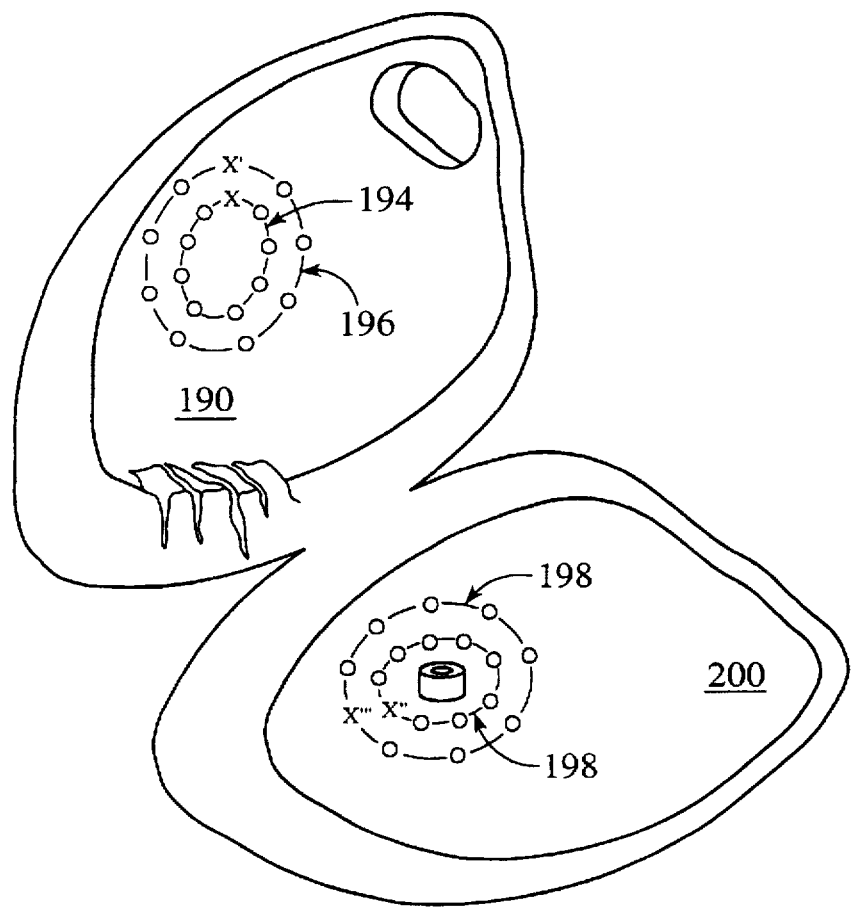
FIG. 6C shows a representative channel hole pattern made with the methods and apparatus of the present invention.

FIG. 6B is a representative cross sectional view of five relative positions of deflection of the laser delivery means 174 of the present invention. FIG. 6C shows a representative channel hole pattern made with the methods and apparatus of the present invention. As described above, with regard to channel formation on a posterior wall 190, once an initial channel denoted by X is created with, for example, the laser delivery means in position 1 of FIG. 6B, the guide means can be rotated a pre-selected amount to a second position to drill a second channel at a different position the same radial distance outward from the trocar. A series of channels 194 can thus be created. Thereafter, it will be apparent that a second series of channels 196 can be created by allowing the distal end of the guide means to be slightly more curved or arched as in position 2 of FIG. 6B as it extends from the distal end of the trocar portion, starting at position X' and rotating the guide means slightly after each channel is bored. Thereafter, much greater curvatures such as position 3 or position 4 can be placed in the distal end of the guide means and a plurality of series of channels 198 can be formed in an anterior wall portion 200 starting with, for example, initial channels at X" and X"', respectively. In summary, various sets of TMR channels can be placed in myocardium from either posterior or anterior walls or other portions of endocardium by drilling a plurality of sets of channels, each set of channels created utilizing embodiments of the present invention with varying, predetermined curvatures imparted to the distal end of the guide means.

Figure 7A:
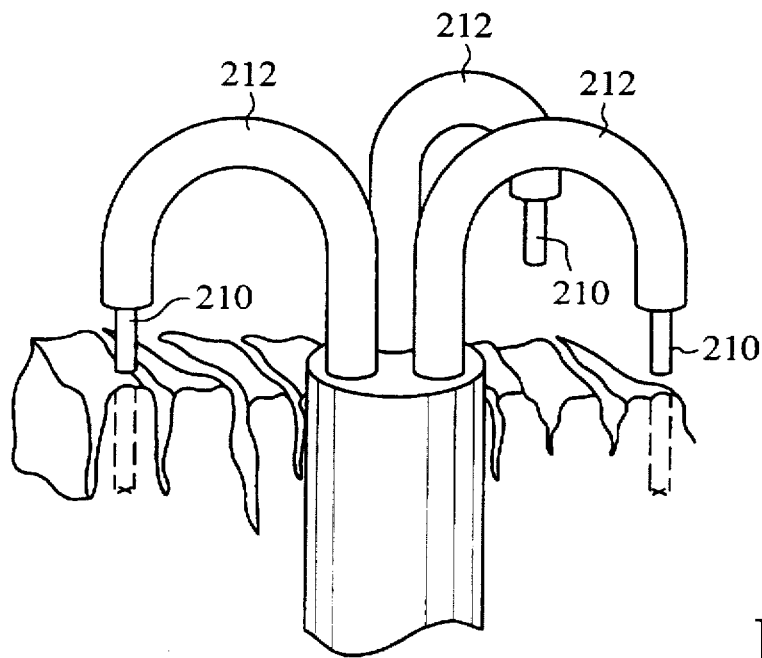
FIG. 7A shows a representative perspective view of an apparatus of the present invention having a plurality of laser delivery means inside a multi-track controllable guide means of the present invention.
Figure 7B:
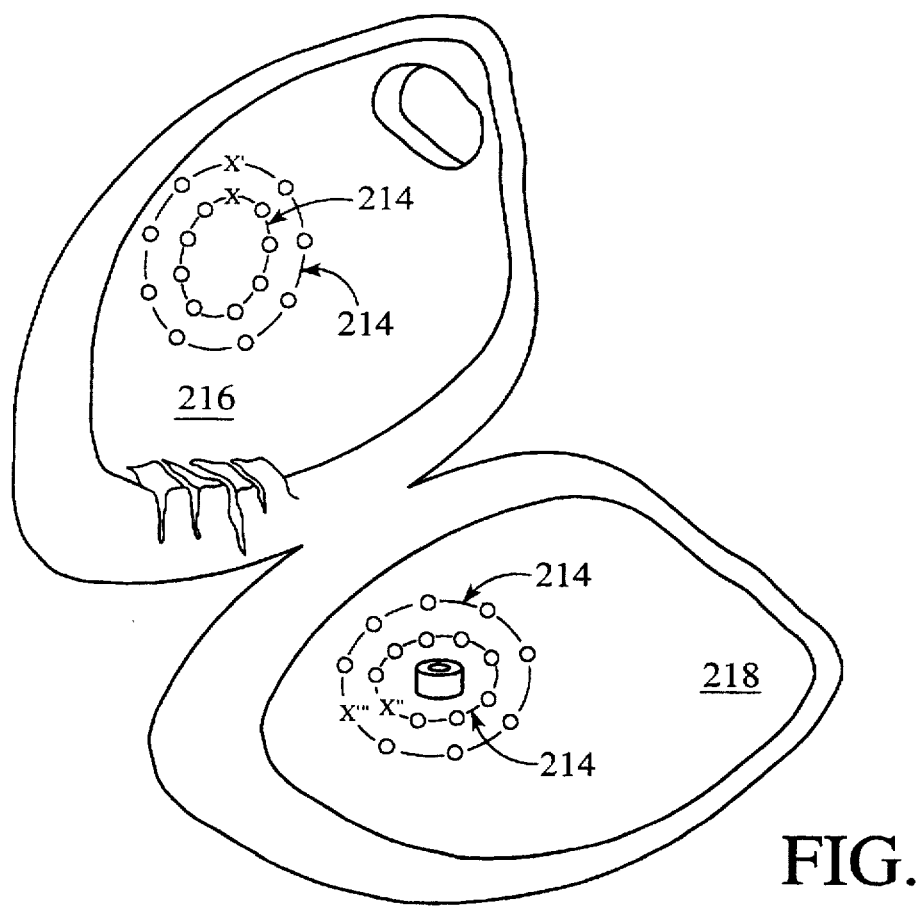
FIG. 7B shows a representative channel hole pattern made with the methods and apparatus of the present invention.

FIG. 7A shows a representative perspective view of an apparatus of the present invention having a plurality of laser delivery means inside a multi-track controllable guide means of the present invention. FIG. 7B shows a representative channel hole pattern made with the methods and apparatus of the present invention. The apparatus has three laser delivery means 210 each disposed within its own respective guide means 212. As described in the foregoing, each guide means can be given a predetermined curvature or orientation so as to deflect its respective laser delivery means to a predetermined angle. Thus, as shown in FIG. 7B, a plurality of sets of TMR channels 214 can be formed starting at posterior walls 216 as well as anterior walls 218 and other areas of endocardium. As described, the guide means is controllable so that the desired deflections of the plurality of laser delivery means 210 can be adjusted precisely and concentric sets of TMR channels are made efficiently and accurately.

Figure 8A:
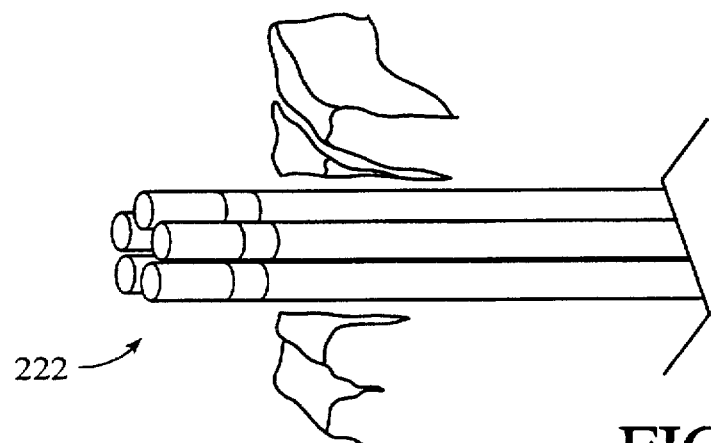
FIGS. 8A, 8B and 8C show representative perspective views of an apparatus of the present invention.
Figure 8B:
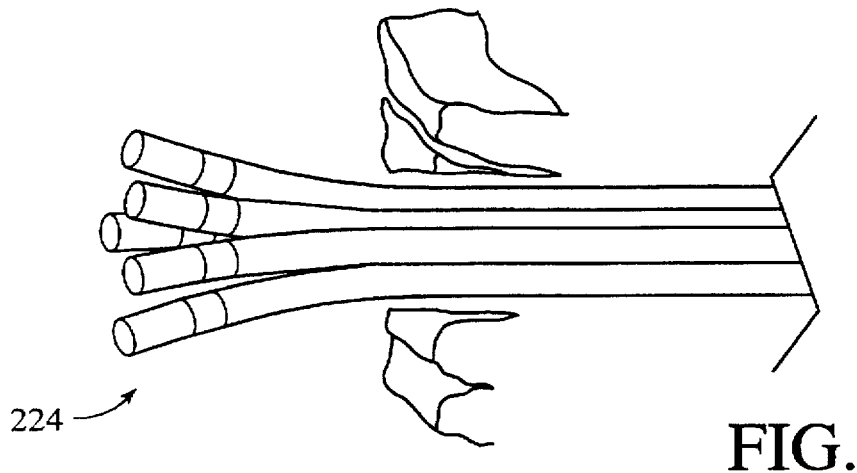
Figure 8C:
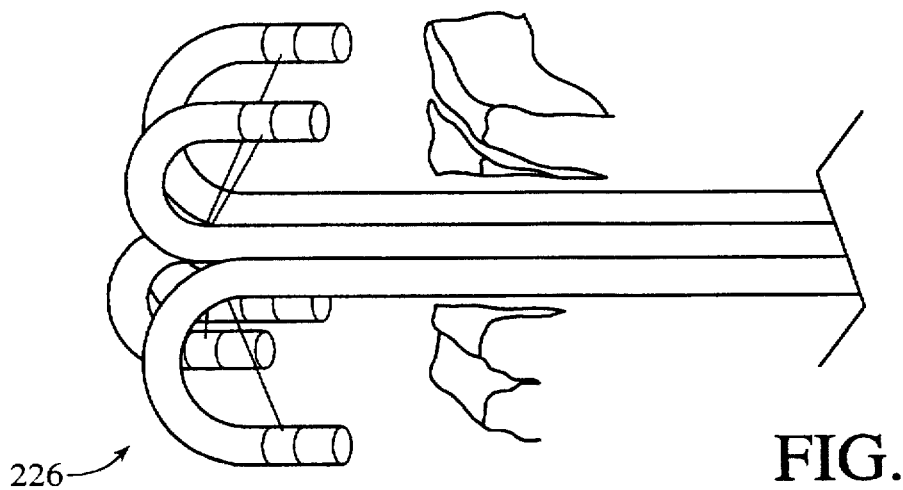

FIGS. 8A, 8B and 8C show representative perspective views of an apparatus of the present invention having five laser delivery means/guide means assemblies in straight 222, slightly deflected 224 and hooked 226 configurations. It will be understood that a greater number of individual guide means and laser delivery means is possible. The laser delivery means typically will be a single optical fiber having a predetermined diameter, a bundle of individual optical fibers, or any other flexible laser light transmitter, whether rotating, apertured and/or focussing system embodiments, etc. It will be understood that providing a greater number of individually controllable laser delivery means may reduce the time required to perform the entire operation, but increase complexity and cost to build.

FIG. 9 is a representative perspective view of a twin fiber single body controllable guide means and trocar apparatus of the present invention. The inner trocar portion 240 is installed through the myocardium 242. An articulating guide means 244 extends from the inner trocar portion. In a preferred embodiment, two individual optical fibers 246, or other laser delivery means including bundles of fibers, extend through the guide means. Each of the two fibers 246 is contained in its own channel which extends through the guide means and can be extended and retracted in the direction shown as G. Alternatively, the individual fibers may be bundled together as they run from the proximal end of the apparatus through the inner trocar and outer trocar, and then be branched through an end cap 248 with a plurality of holes or deflecting channels built therein. It will be understood that alternate embodiments include three or more individually extendable and retractable optical fibers, fiber bundles or other laser delivery means.

Articulation and other control of the guide means is effected in a number of ways. In a preferred embodiment, a plurality of steering wires 250 run axially through the guide means being disposed toward the outer surfaces of the guide means. A flexible spine 252 of the guide means is formed in a number of ways, such as by removing certain material along the outside of the guide means so as to permit flexing of the guide means into an arc with a predetermined radius H. Other methods of forming the flexible portion include the use of flexible braided tubing, accordion-type wall structure, etc. It will be obvious to those skilled in the art that using the steering or tensioning wires in the familiar "push" or "pull" manner will allow the surgeon to easily and effectively form a curvature in the distal end of the guide means oriented to precisely the position desired. The apparatus also comprises a rotating mechanism 254 which will allow the guide means to be rotated in a predetermined manner. In a preferred embodiment, this rotating mechanism is indexed, giving full 360 degree rotation.

FIGS. 10A and 10B are representative perspective views of a multi-guide means TMR trocar apparatus of the present invention. In a preferred embodiment, three guide means 260 are each comprised of individually articulating, molded flexible spines 262 at one end. The three spines are clustered together and originate from inner trocar 264. The individual flexible spines will be attached to the trocar or will be extendable and retractable inside the trocar. In either event, bundles of fibers 266, or other laser delivery means including individual optical fibers, can be individually advanced through the guide means in the direction shown as I. In a preferred embodiment, the trocar houses the tissue piercing means such as a three-bladed piercing tip. In such case, the apparatus is initially assembled such that the flexible spines are retracted into the inner trocar. As the hole is created, the trocar is placed in the heart wall. The blade can be retracted into the trocar through opening 267. Thereafter, the individual guide means can be extended therethrough. They are oriented such that steering or tensioning wires 268 are located toward the perimeter of the trocar or the outside of the assembly, each symmetric with one another. In this configuration, the cluster of three guide means extending through the trocar will provide a means for delivering three individually controllable laser delivery means to a posterior wall 270 or other portion of endocardium. As channels are formed, the angular orientation of the guide means in direction J can be adjusted as desired. At a maximum, the guide means will deflect the laser delivery means, such as the optical fiber or fiber bundle, backward into myocardium of an anterior wall 272 or other portion of heart tissue. This arching of the spines is caused by retraction of the steering wires in the direction shown as K. Perpendicular or substantially perpendicular surfaces 274 of the distal ends of the articulating flexible spines 262 preferably are oriented about 90° to the laser delivery fiber 266, thereby acting as a depth stop to the fiber when inserted into myocardium.

Figure 11A:
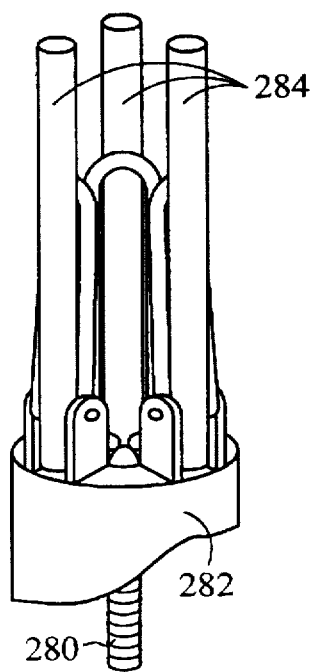
FIGS. 11A, 11B and 11C are representative perspective and cross sectional views of a cantilevered fiber positioning linkage with lever TMR trocar apparatus of the present invention.
Figure 11B:
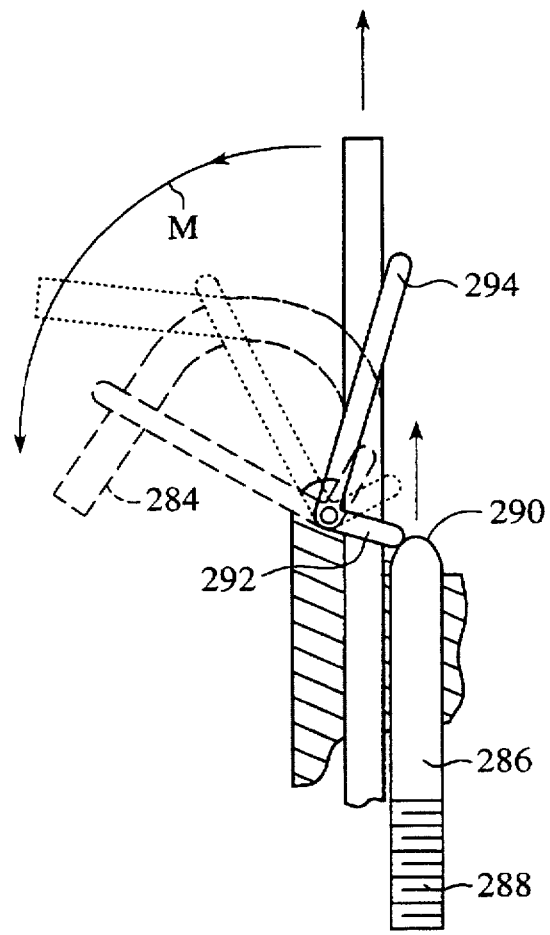
Figure 11C:
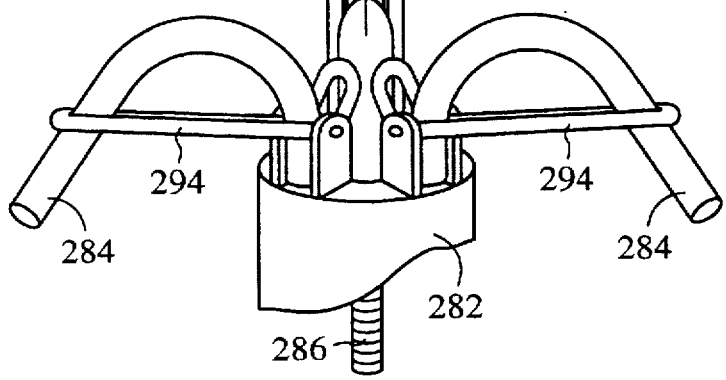

FIGS. 11A, 11B and 11C are representative perspective and cross sectional views of a cantilevered fiber positioning linkage with lever TMR trocar apparatus of the present invention. The obturator 280 comprises a three-channeled guide means 282, each channel for containing a single optical fiber, fiber bundle or other laser delivery means 284. A central extendable shaft 286 can be extended or retracted a precise amount. A preferred embodiment comprises a micro metering mechanism 288 for fine adjustment of the deflection of the laser delivery means. As the central shaft 286 is moved in the direction shown as L, a bearing surface 290 is brought to bear on levers 292, having the effect of pivoting cantilevered deflection brackets 294 in direction M. As described in the foregoing, an essentially infinite number of positions for deflection of the fibers are possible, although it will be apparent to known to those skilled in the art that a discrete number of channels spaced efficaciously will be the optimum method of using the apparatus of the present invention.

Figure 12A:
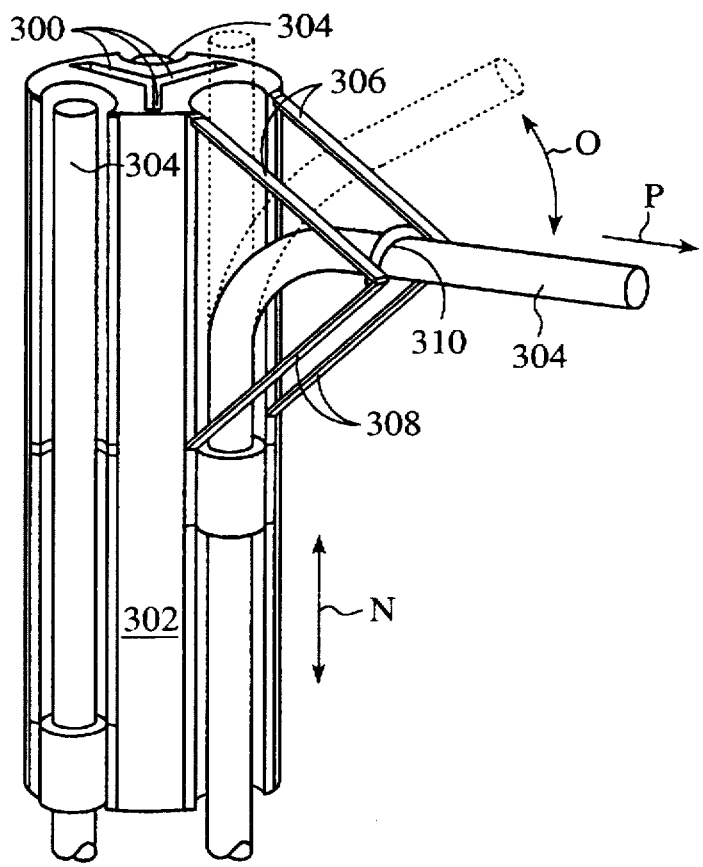
FIGS. 12A and 12B are representative perspective views of a pumped-type fiber positioning linkage TMR trocar apparatus of the present invention.
Figure 12C:
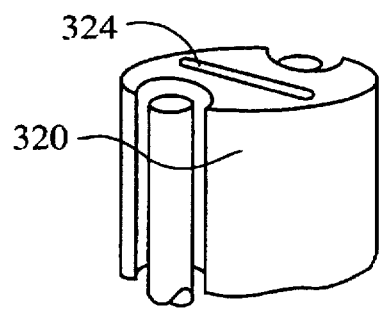
FIGS. 12C and 12D are representative perspective views of obturator means for TMR trocar apparatus of the present invention.
Figure 12D:
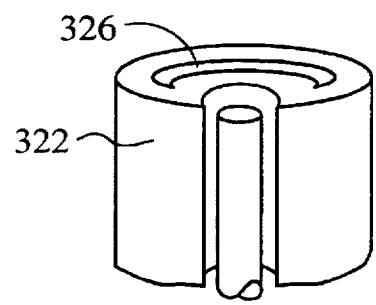
Figure 12B:
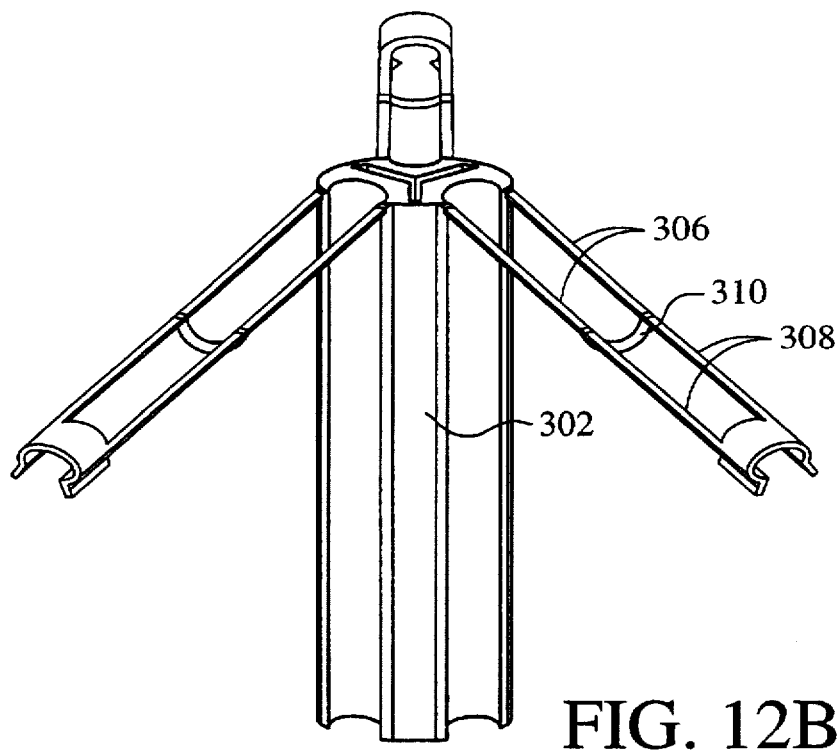

FIGS. 12A and 12B are representative perspective views of a pumped-type fiber positioning linkage TMR trocar apparatus of the present invention. The obturator 300 comprises a three-channeled guide means 302, each channel for containing a single optical fiber, fiber bundle or other laser delivery means 304. As the linkage is given linear motion in direction N, upper and lower linkages 306 and 308, respectively, are raised radially and in unison from the guide means, causing deflection collar 310 to deflect the laser delivery means in direction O. A preferred embodiment of the linkage is molded as a one piece unit, as shown pre-assembly in FIG. 12B. Suitable materials of construction will be inexpensive and sterilizable, and will include metals, plastics, rubbers, etc.

FIGS. 12C and 12D are representative perspective views of obturator means for TMR trocar apparatus of the present invention. In contradistinction to the foregoing, a dual fiber guide means 320 and a single fiber guide means 322 both have fiber channels which run along the outer surface of the obturator means. Slot 324 serves as a guide for a retractable tissue piercing means, such as a flat razor-sharp blade, for gaining entrance to the inside chamber of the heart. Slot 326 is curved and serves as a guide for a curved tissue piercing means. In both embodiments, it will be understood that the tissue piercing means is retractable and is either built into the obturator means or is removable. In either case, appropriate blood seal means will be used.

Figure 13A:
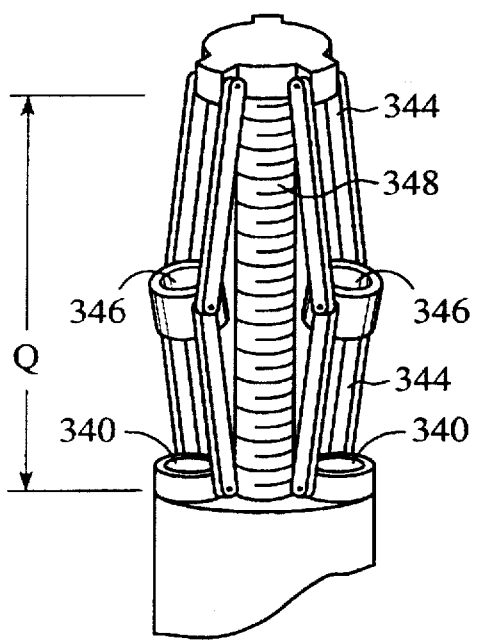
FIGS. 13A and 13B are representative perspective views of a scissors jack-type fiber positioning linkage TMR trocar apparatus of the present invention.
Figure 13B:
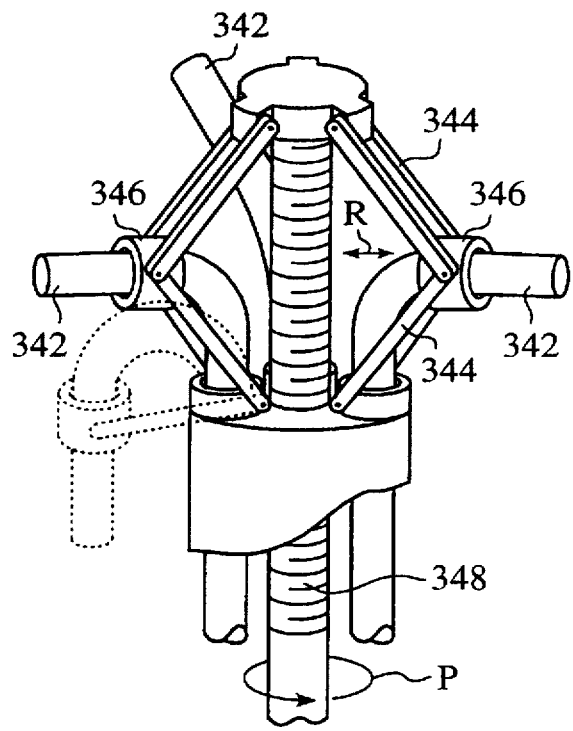

FIGS. 13A and 13B are representative perspective views of a scissors jack-type fiber positioning linkage TMR trocar apparatus of the present invention. This guide means has three channels 340 for directing and deflecting laser delivery means 342 as desired. Jack linkages 344 connect together at deflection collar 346. An advancing and retractable screw member 348 rotated in direction P, thereby shortening distance Q between the unconnected ends of the linkages and forcing them outward in direction R. This causes deflection collar to deflect the plurality of laser delivery means to the side. In this manner, as the advancing screw member is rotated to shorten the distance between the linkages, the laser delivery means will be deflected into predetermined positions for creating multiple channels in posterior and anterior walls and other structures within heart chambers. It will be understood by those skilled in the art that the scissor jack-type fiber positioning linkage assembly as shown and described is but one embodiment of a large number of similarly possible apparatus, and which are all included in the scope of the present invention.

Figure 14:
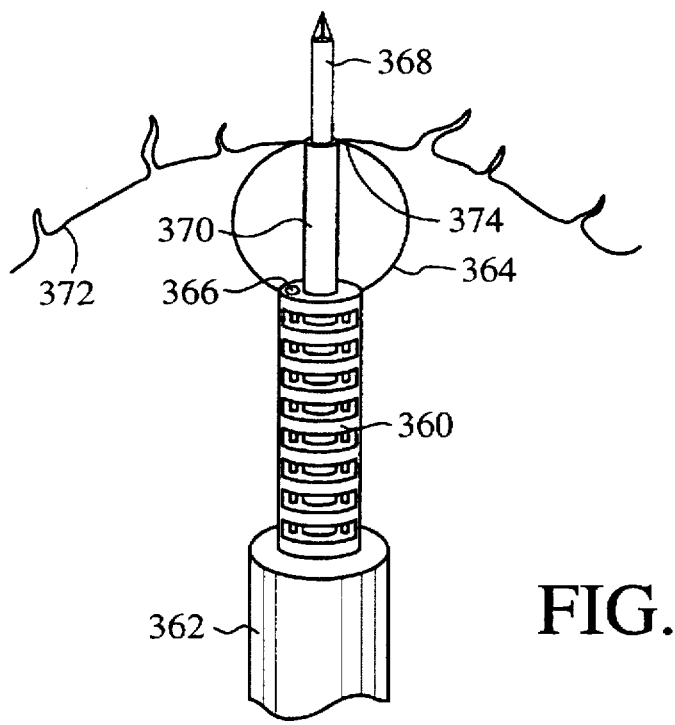
FIG. 14 is a representative perspective view of a balloon end controllable TMR trocar apparatus of the present invention.

FIG. 14 is a representative perspective view of a balloon end controllable TMR trocar apparatus of the present invention. As described, an articulating guide means 360 is disposed within and extends from the trocar portion 362. A balloon scope portion 364 is attached to the guide means at its distal end. Access port 366 provides access to the interior of the balloon scope portion. The port can be used to introduce a visualization scope, other visualization means including ultrasonic imaging, or other equipment into the interior of the balloon scope portion. To pass the laser delivery means 368 through the balloon scope portion, a hollow tubular channel structure 370 is provided between the end of the guide means and the opposite side of the balloon scope portion. Thus, as the balloon scope portion is pressed against the endocardium 372, visualization of the advancing laser delivery device through the TMR channel site 374 can be achieved. Control means for the fiber deflection guide means will also be available, including steering or tensioning wires, pre-curved tubing, etc. Preferred embodiments include additional features which will be apparent to those skilled in the art, including additional laser delivery means and associated hollow tubular channel structures, balloon fill and/or evacuation ports, etc.

Figure 15A:
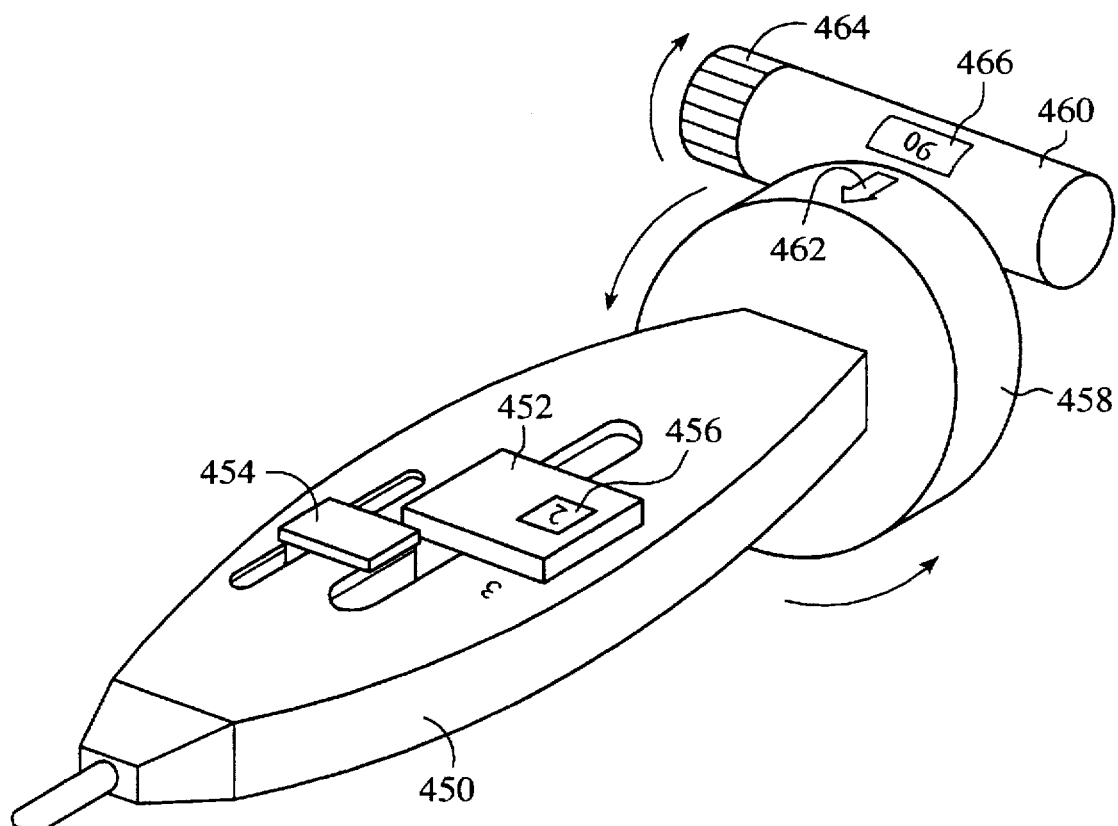
FIGS. 15A and 15B are representative perspective and cross sectional views of a preferred embodiment of an external handle for use in fiber rotation and advancement control for the present invention.
Figure 15B:
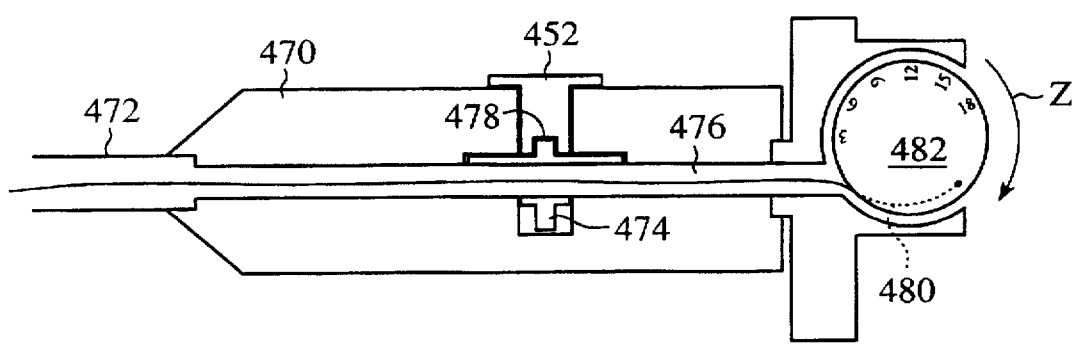

FIGS. 15A and 15B are representative perspective and cross sectional views of a preferred embodiment of an external handle for use in fiber rotation and advancement control for the present invention. The handle portion 450 is shaped to fit in the surgeon's hand. The central portion of the handle allows the surgeon to advance the fiber by means of advancement lever 452. This lever can be positioned accurately using an adjustable stop mechanism 454 to provide accurate and optimum depth positioning of the fiber. In a preferred embodiment, a visualization window 456 clearly indicates to the surgeon the depth to which the fiber can be advanced according to the current depth stop settings. The distal portion of the handle houses a fiber rotation control means 458 and a fiber angulation control means 460. The fiber rotation control means permits the surgeon to rotate the fiber, fibers or fiber bundles about their central axes, with relative rotation indicated by arrow indicator 462. Fiber angulation control means also has a rotating knob 464 which allows the surgeon to adjust the degree of deflection of the distal ends of the laser delivery means. A visualization window 466 in conjunction with a metering type of assembly will give the surgeon an awareness of the precise angle of deflection of the fibers.

The distal end 470 of the handle portion is connected at point 472 to the trocar apparatus. Tabs 474 on the fiber 476 prevent the fiber from slipping through the handle. The advancement lever 452 also has a slot 478 which will allow 360° rotation of the laser delivery means. In a preferred embodiment, tensioning guide wires 480 extend through the handle back to the fiber angulation control means, and connect to a rotating drum 482, allowing manual control of the guide wires. Thus, as the angulation control means is adjusted, for example by rotation in a direction shown as Z, the guide wires are pulled or pushed and the desired deflection or angulation of the distal ends of the laser delivery means is achieved.

Such laser delivery means advancement and rotation control means of the present invention are more fully described in co-pending U.S. patent application Ser. No. 08/675,698, filed concurrently herewith.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A minimally invasive surgical (MIS) apparatus for providing access to the chambers of an active heart and performing procedures therein by insertion through a chest wall and through a myocardium, the apparatus comprising:

a trocar having a proximal end for positioning on the outside of the chest wall and a distal end for inserting through the myocardium, the trocar includes means for
   a) sealing fluids within the chest wall and heart and
   b) stopping blood flow from the trocar's lumen;

a laser means for delivering laser energy to a procedural site, the laser means inserts and translates through the sealing means for stopping blood flow from the trocar's lumen; and guide means for orienting the laser means distal end at the procedural site.

2. The surgical apparatus of claim 1 the trocar's distal end includes a tissue piercing means for cutting an opening in the heart's epicardium for inserting the trocar into the myocardium.

3. The apparatus of claim 2 wherein the trocar includes a chest wall proximal portion and a heart distal portion with a flexible section there between, the chest wall portion has an opening and is configured for positioning on and insertion through a chest wall, and the heart distal portion is configured for passing through the trocar's chest wall portion and insertion through the heart's myocardium.

4. The apparatus of claim 3 wherein the heart distal portion includes the means for stopping blood flow from the trocar's lumen.

5. The apparatus of claim 3 wherein the trocar's chest wall portion is separable from the heart distal portion.

6. The apparatus of claim 2 wherein the piercing means can retract into the trocar's distal end.

7. The apparatus of claim 6 wherein the guide means includes an extendible and deflectable shaft that surrounds the laser means.

8. The apparatus of claim 2 wherein the tissue piercing means is an obturator attached to the distal end of the trocar and has an externally ribbed shaft thereby stabilizing the trocar when implaced.

9. The apparatus of claim 2 wherein the tissue piercing means is an obturator slidably disposed within the distal end of the trocar.

10. The apparatus of claim 1 wherein the means for stopping blood flow from the trocar's lumen is an annular housing with an inner housing portion with coaxially aligned
   a) elastic slit seal and
   b) round seal with a center void, the laser means inserts through the slit and round seals.

11. The apparatus of claim 1 wherein the means for stopping blood flow from the trocar's lumen is an annular housing with an inner housing portion with a hinged door member attached to an inside wall portion of the housing portion.

12. The apparatus of claim 1 wherein the laser means includes at least one optical fiber element and a laser source selected from the group consisting of Holmium (HO:YAG) and Excimer type lasers.

13. The apparatus of claim 12 wherein the at least one optical fiber element is comprised of multiple optical fiber strands.

14. The apparatus of claim 1 wherein the guide means includes at least one curved rotatable tube surrounding the laser means and is extendable beyond the trocar's distal end.

15. The apparatus of claim 14 wherein the curved tube is made from shape memory material.

16. The apparatus of claim 1 wherein the guide means comprises:

an articulating portion extending beyond the trocar's distal end, the articulating portion having proximal and distal ends, the proximal end is adjacent the distal end of the trocar; and control means for bending the articulating portion, thereby orienting the laser means at the procedural site.

17. The apparatus of claim 16 in which the laser delivery means is slidably positioned within the articulating portion of the guide means, the distal end of the laser means is extendable beyond the distal end of the articulating portion.

18. The apparatus of claim 16 in which the control means of the guide means is a steering wire whereby pushing and pulling on the steering wire causes the articulating portion to bend and effectuate orientation of the laser means.

19. The apparatus of claim 1 wherein the guide means comprises at least one rotatable, hollow tube surrounding the laser means, the laser means having a distal end pre-bent into a curved position within the hollow tube, the distal end maintaining the curved position when advanced out of the hollow tube into the chambers of the heart.

20. The apparatus of claim 1 further comprising fiber rotation control means for controlling the angular rotation of the laser means.

21. The apparatus of claim 1 further comprising fiber angulation control means for controlling the orientation of the distal end of the laser means.

22. The apparatus of claim 1 further comprising a handle portion, the handle portion including the fiber rotation control means for controlling the angular rotation of the laser means and fiber angulation control means for controlling the angular rotation of the laser means.

23. A minimally invasive surgical method for performing a revascularizing procedure through a chest on an active heart's endocardium, the method comprising the steps of:

a) positioning a trocar device with a means for:
   i) sealing fluids within the chest wall and the heart and
   ii) stopping blood flow from the trocar's lumen, through the chest's wall;

b) creating an opening for the trocar device on the heart's outer surface;

c) positioning the trocar device through the heart's myocardium and into the heart's chamber;

d) moving at least one laser delivery device through the trocar device and the means for stopping blood flow from the trocar's lumen, and into the heart's chamber; and e) delivering laser energy from the at least one laser energy delivery device.

24. The method of claim 23 further comprising a step of suturing the trocar device's opening prior to placing the trocar device into the heart's chamber.

25. The method of claim 23 further comprising a step of moving the laser delivery means through the heart's chamber, across a heart valve, and into an adjacent heart chamber.

26. The method of claim 23 wherein the step e) includes forming of a plurality of channels from the heart's endocardium into the myocardium by moving a plurality of laser delivery devices simultaneously.

27. A trocar for performing minimally invasive surgery (MIS) on an active heart comprising:

a proximal end configured to protrude outwardly from a chest wall and defining a cavity;

means for sealing fluids within the chest wall and heart;

means for sealing blood flow from the trocar's lumen;

a distal end defining means for penetrating a heart's epicardium for inserting the distal end through myocardium and into the heart's ventricle; and hollow connector means for permitting passage of surgical tools from outside the chest wall into the heart's chamber, the sealing means for stopping blood flow from the trocar's lumen is connected to the connector means and allows passage of the surgical tools.

* * * * *